United States Patent [19]

Mueller

[11] Patent Number: 4,587,367

[45] Date of Patent: May 6, 1986

[54] PROCESS FOR THE PRODUCTION OF DICHLOROISOBUTENES

[75] Inventor: Dieter J. Mueller, Marl, Fed. Rep. of Germany

[73] Assignee: Huels Aktiengesellschaft, Marl, Fed. Rep. of Germany

[21] Appl. No.: 727,177

[22] Filed: Apr. 25, 1985

[30] Foreign Application Priority Data

Apr. 25, 1984 [DE] Fed. Rep. of Germany ....... 3415335

[51] Int. Cl.$^4$ ............................................ C07C 17/06
[52] U.S. Cl. .................................................... 570/216
[58] Field of Search ......................................... 570/216

[56] References Cited

U.S. PATENT DOCUMENTS 2,189,890  2/1940  Engs et al. ........................... 570/234
2,380,500  7/1945  Buc et al. ............................. 570/234

OTHER PUBLICATIONS

JACS 68, 787 (1946).

*Primary Examiner*—Charles F. Warren
*Assistant Examiner*—Joseph A. Boska
*Attorney, Agent, or Firm*—Millen & White

[57] ABSTRACT

Cis- and trans-1,3-dichloro-2-methylpropene and 3-chloro-2-chloromethylpropene are produced by the reaction of 3-chloro-2-methylpropene with sulfuryl chloride in the presence of catalytic amounts of amines and/or phosphines.

14 Claims, No Drawings

PROCESS FOR THE PRODUCTION OF DICHLOROISOBUTENES

CROSS REFERENCE TO RELATED APPLICATIONS

This application is related to commonly assigned U.S. application Ser. No. 727,176, filed 4/25/85, and also Ser. Nos. 644,418 and 644,466, both of Aug. 27, 1984, which disclosures are incorporated by reference herein.

BACKGROUND OF THE INVENTION

This invention relates to a process for the production of dichloroisobutenes, namely cis- and trans-1,3-dichloro-2-methylpropene and 3-chloro-2-chloromethylpropene.

Among the aforementioned products, 3-chloro-2-chloromethyl-propene, in particular, is of interest as an intermediate for a number of organic syntheses, i.e., for the syntheses of crown ethers (C. A. 90 (1979), p. 644, 90: 121561 a; C. A. 93 (1980), p. 697, 93: 204708 s) while cis- and trans-1,3-dichloro-2-methyl-propenes are used as molecular weight controllers in a polymerization reaction, or nematocides (C. A. 77 (1972), p. 22, 75779 j; molecular weight controller; C. A. 93, (1980), p. 192, 93: 127082 d, nematocides) and also utilized for further chlorination.

According to East German Pat. No. 106,345, the aforementioned dichloroisobutenes can be manufactured by the gas-phase chlorination of isobutene at 60°–80° C. Using an isobutene/chlorine ratio of 0.4 to 0.5, there is obtained about 30% of 1,3-dichloro-2-methylpropene, 30% of 3-chloro-2-chloromethylpropene, 30% of 1,2,3-trichloro-2-methyl-propane, and 10% of 3-chloro-2-methylpropene.

In other known manufacturing methods, 3-chloro-2-methylpropene is further chlorinated with chlorine at low temperatures. Under controlled conditions, there is obtained about 25–30% of 3-chloro-2-chloromethylpropene, 25% of 1,3-dichloro-2-methylpropene, 30% of 1,2,3-trichloro-2-methylpropane, together with other higher-chlorinated products (Z. Chem. 8 [1968]6: 220–221; J. Am. Chem. Soc. 69: 2 614–2 616 [1947]; and Chem. Abstr. 63: 4 148 [1965]).

The further chlorination of 3-chloro-2-methylpropene with $SO_2Cl_2$ is reported to give an 83% yield of 1,2,3-trichloro-2-methylpropane (J. Am. Chem. Soc. 68: 787 [1946]).

These prior art processes for the production of dichloroisobutenes generally give rise to appreciable quantities of undesired by-products.

SUMMARY OF THE INVENTION

It is therefore an object of the present invention to provide an improved process for the manufacture of dichloroisobutenes.

It is a further object of the invention to provide a process which is feasible in operation and which produces increased yields of dichloroisobutenes.

Upon further study of the specification and appended claims, further objects and advantages of this invention will become apparent to those skilled in the art.

It has now been discovered that the further chlorination of 3-chloro-2-methylpropene with $SO_2Cl_2$ in the presence of amines and/or phosphines, unexpectedly and contrary to what has been described in the literature for the uncatalyzed reaction, yields predominantly substitution products, such as cis- and trans-1,3-dichloro-2-methylpropene and 3-chloro-2-chloromethylpropene.

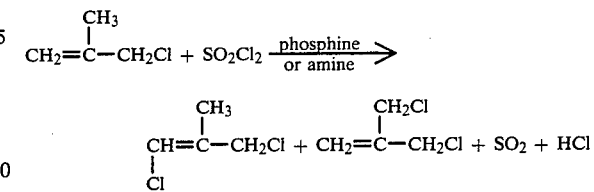

The combined yield of dichloroisobutenes obtained is about 70–80%.

DETAILED DISCUSSION

The process of the invention is preferably conducted in the liquid phase. It was found expedient to heat 3-chloro-2-methylpropene, after addition of the amine or phosphine catalyst, to a starting temperature of 30°–65° C., and then to add sulfuryl chloride in metered, preferably less than stoichiometric quantities, e.g., 65–95%. It is noted that the presence of equivalent or more than stoichiometric amounts of $SO_2Cl_2$ does not impede the course of reaction. However, in such a case, work up of the reaction mixture becomes more difficult since the separation of unreacted $SO_2Cl_2$ is more difficult than the separation of unreacted 3-chloro-2-methylpropene.

In the presence of the amine or phosphine catalyst, the substitution reaction is highly exothermic and very rapid. Thus, it is advantageous to feed $SO_2Cl_2$ to the reaction mixture at the same rate as it is consumed by the reaction. The course of the reaction can be monitored by observing the rate of formation of the gaseous $SO_2$ and HCl evolved.

The temperature of the reaction mixture can rise up to its boiling point. The heat of reaction can be removed by external cooling of the reaction vessel or by means of a cooled reflux condenser.

The reaction can be performed discontinuously, for example, in an agitated vessel, as well as continuously, for example, in a tubular reactor or a cascade.

Suitable catalysts for the reaction are amines or phosphines or derivatives thereof.

For example, such compounds include primary, secondary or tertiary amines, e.g., aliphatic amines, such as diisopropylamine, triethylamine, tributylamine (mono-, di- or tri-$C_{1-10}$-alkyl)amines, or aromatic amines, such as diphenylamine, benzidine or toluidines, or heterocyclic amines, such as pyridine, picolines, pyrrole, pyrazole, quinoline, carbazole or quinaldine. It is also possible to use combinations of several nitrogen-containing bases, the above listing being merely exemplary. Pyridine, picoline, diisopropylamine, triethylamine and/or quinoline are preferably used. But also other than the above mentioned N-containing organic compounds may be useful such as amides like urea, substituted ureas or compounds such as hydrazines like diethylhydrazine or even hydrazones.

The aliphatic or aromatic (primary, secondary or tertiary) phosphines can also be employed. Especially suitable are aliphatic phosphines, e.g., those corresponding to the amines disclosed above. Also, the combinations of several phosphines as well as combinations of amines with phosphines are suitable. Aromatic phosphines are also suitable, e.g., those corresponding to the amines discussed above. Triphenylphosphine and/or tributylphosphine are preferably used. But also other P-containing organic compounds may be useful as catalysts such as phosphinoxides like triphenylphosphinoxide or P,P-dichlorophenylphosphine.

Usually, about 1–10,000 ppm of these compounds per weight of 3-chloro-methylpropene is sufficient to catalyze the desired reaction. Preferably, >10 to 10,000, especially 100–1,000 ppm is employed. Since, in many cases, chlorinated hydrocarbons are stabilized with amines, 3-chloro-2-methylpropene, stabilized in this way, may even react in the desired way without the necessity for the introduction of additional amine or phosphine catalyst.

The reaction takes place generally at a temperature of 30°–70° C., preferably 45°–65° C. in a time period of 60–180 minutes, preferably 90–120 minutes. $SO_2Cl_2$ is added in measured portions generally over a period of 10–90 minutes, preferably 30–60 minutes.

The reaction product is fractioned to isolate dichloroisobutene product. When distillation at atmospheric pressure is utilized, the desired products have a boiling range of 131°–133° C. (cis/trans-1,3-dichloro-2-methylpropene) and a boiling range of 137°–139° C. (3-chloro-2-chloromethylpropene). However, fractionation is preferably performed under reduced pressure to minimize the possibility of thermal decomposition.

The yields of the aforementioned, unsaturated dichloroisobutenes range generally between 70% and 80%, based on the amount of 3-chloro-2-methylpropene reacted.

Light can shift the course of the reaction from substitution toward addition, and the process is suitably conducted under exclusion of light, i.e., at a wavelength of 200–400 nm and more generally, e.g. at 185–500 nm. See Ser. No. 644,466, and Ser. No. 727,176, filed 4/25/85 above. For reasons also explained in these cited applications, it is also preferred to avoid the presence of aldehydes where their presence is a potentiality.

It is also possible to conduct the reaction in solvents, e.g., $CCl_4$ or other inert diluents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

An agitator-equipped reactor with reflux condenser and dropping funnel is charged with 90.6 g of freshly distilled 3-chloro-2-methylpropene, combined with a nitrogen or phosphorus compound according to Table 1, heated to 45° C., and then, in total, 108 g of sulfuryl chloride is added in metered quantities to the stirred reaction mixture over a period of 30–90 minutes. During the oxidation step, the temperature of the reactor is maintained in a range of between 45° and 50° C. controlled with the aid of a thermostat. The gaseous by-products, $SO_2$ and HCl, formed during the reaction, are removed via the reflux condenser and absorbed in a river with water made alkaline to pH 9.5. The pH value is maintained constant by automatic titration with a sodium hydroxide solution of defined concentration so that the progress of the reaction can be monitored by means of the consumption of sodium hydroxide solution. The rates of sulfuryl chloride conversion ranges between 90 and 98%, using reaction periods of 90 minutes to 180 minutes.

The amount of product obtained ranges between 120 and 135 g. The crude product, after washing in water and drying over $K_2CO_3$, is subjected to analysis by gas chromatography. The composition of the product obtained can be seen from Table 1 (unreacted 3-chloro-2-methylpropene is not included in the calculation).

TABLE 1

Examples for the Catalytic Reaction of 3-Chloro-2-methylpropene with $SO_2Cl_2$ in the Presence of Organic Nitrogen Compounds and Phosphorus Compounds, Present as Amines and Phosphines

| | Amine and/or Phosphine as Catalyst | ppm | Reaction Temperature °C. | Metered Feeding Period $SO_2Cl_2$ min | Reaction Period min | Amount of Crude Product g | Composition of Pure Product % | | |
|---|---|---|---|---|---|---|---|---|---|
| | | | | | | | 1,2,3-Tri-chloro-2-methyl-propane | cis/trans-1,3-Di-chloro-2-methyl-propene | 3-Chloro-2-chloro-methyl-propene |
| 1 | Diisopropyl-amine | 100 | 45–50 | 30 | 90 | 125 | 27.5 | 35.5 | 36.5 |
| 2 | Tributyl-amine | 1,000 | 45–50 | 30 | 90 | 124 | 23.0 | 37.0 | 39.0 |
| 3 | Tributyl phosphine | 1,000 | 45–50 | 60 | 150 | 124 | 23.0 | 37.5 | 38.5 |
| 4 | Pyridine | 1,000 | 45–50 | 30 | 120 | 135 | 23.5 | 37.5 | 38.0 |
| 5 | Quinaldine | 1,000 | 45–50 | 60 | 120 | 128 | 31.0 | 33.0 | 35.0 |
| 6 | Carbazole | 1,000 | 45–50 | 90 | 180 | 125 | 22.0 | 38.0 | 40.0 |
| 7 | Triphenyl phosphine | 1,000 | 45–50 | 60 | 150 | 120 | 25.0 | 37.0 | 37.0 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of 1,3-dichloro-2-methylpropene and 3-chloro-2-chloromethylpropene which comprises reacting 3-chloro-2-methylpropene with sulfuryl chloride in the presence of a catalytically effective amount of an amine or a phosphine.

2. A process according to claim 1, wherein the reaction is conducted in the liquid phase.

3. A process according to claim 2, wherein the reaction is conducted at a temperature of 30°–70° C. and at atmospheric pressure.

4. A process according to claim 3, wherein the temperature is 45°–65° C.

5. A process according to claim 1, wherein the reaction is conducted in the essential absence of light.

6. A process according to claim 1, wherein sulfuryl chloride is added to 3-chloro-2-methylpropene and the amine or the phosphine in metered quantities.

7. A process according to claim 6, wherein the sulfuryl chloride is added at the rate it is consumed during the reaction.

8. A process according to claim 6, wherein less than a stoichiometric amount of sulfuryl chloride, relative to 3-chloro-2-methylpropene, is added.

9. A process according to claim 1, wherein the amine or phosphine is present in a concentration range from 1 to 10,000 ppm by weight based on 3-chloro-2-methylpropene.

10. A process according to claim 1, wherein the amine or phosphine is present in a concentration range from 100 to 1,000 ppm by weight based on 3-chloro-2-methylpropene.

11. A process according to claim 9, wherein the amine is an aliphatic, aromatic or heterocyclic amine.

12. A process according to claim 9, wherein the phosphine is an aliphatic or aromatic phosphine.

13. A process according to claim 9, wherein the catalyst is a mixture of amine and phosphine.

14. A process of claim 9, wherein the catalyst is pyridine, picoline, diisopropylamine, triethylamine or quinoline.

* * * * *